(12) United States Patent
Stanger (10) Patent No.: US 7,138,554 B2
(45) Date of Patent: Nov. 21, 2006

(54) SYNTHESIS OF (DIBROMOCYCLOBUTA) AROMATIC COMPOUNDS

(75) Inventor: Amnon Stanger, Haifa (IL)

(73) Assignee: Technion Research and Development Foundation, Haifa (IL)

( * ) Notice: Subject to any disclaimer, the term of this patent is extended or adjusted under 35 U.S.C. 154(b) by 250 days.

(21) Appl. No.: 10/472,180

(22) PCT Filed: Jun. 12, 2002

(86) PCT No.: PCT/US02/18251

§ 371 (c)(1),
(2), (4) Date: Sep. 22, 2003

(87) PCT Pub. No.: WO02/102810

PCT Pub. Date: Dec. 27, 2002

(65) Prior Publication Data

US 2004/0116755 A1    Jun. 17, 2004

(51) Int. Cl.
*C07C 17/00* (2006.01)
(52) U.S. Cl. .................. 570/190; 570/201; 570/202; 570/212; 570/215
(58) Field of Classification Search ............... 570/101, 570/190, 201, 202, 212, 213, 215
See application file for complete search history.

(56) References Cited

OTHER PUBLICATIONS

Chemistry—European Journal, (1997), 3(2), 208-211.*

"Polyacene and a new class of quasi-one-dimensional conductors" Kivelson et al, O.L. *Phys. Rev.* 1993, b28, 7326.

"A Study On The Pristine And The Doped Polyacenic Semiconductive Materials" Tanaka et al, *Synth. Metals* 1984, 9, 41.

"An Approach To The Preparation Of Polyacene by LB Method". Ozaki et al, . *Synth. Metals* 1989, 28 C801.

"Nickel-Mediated Cyclobutabenzene Syntheses trans-7, 8-Dibromocyclobutabenzenes Their one pot preparation, X-Ray Structure and Diels-Alder Reactions" Stanger et al, *J Org. Chem.* 1996, 61, 2549.

"Hexabromotricyclolbutabenzene and Hexabromohexaradialene: Their Nickel-Mediated One-Pot Syntheses and Crystal Structures" Stanger et al, *Chem. Eur. J.* 1997, 3, 208.

"Nickel Mediated Cyclobutabenzenes Syntheses" Stanger et al. in *Organic Synthesis via Organometallics OSM 5*, Helmchen, G.; Dibo J.; Flubacher, D.; Wiese, B.: Eds. Friedrich Vieweg & Sohn Verlags GmbH, Braunschweig/Wiesbaden, 1997, pp. 59-66.

"Cyclobutarenes Part 3, Synthesis of Bromodicyclobutarenes and Some New Derivatives of the Benzocyclobutabiphenylenes" Shepherd et al, *Chem. Soc. Perkin Trans. I* 1988, 961.

* cited by examiner

*Primary Examiner*—J. Parsa
(74) *Attorney, Agent, or Firm*—Mark M. Friedman (57) ABSTRACT

A method for the synthesis of cyclobuta aromatic compounds by cyclizing two ortho dibromoalkyl substituents is described. Using a mediator, such as nickel metal, and continuous removal of product from contact with the mediator, high product yields are achieved. A method for bromination of ortho alkyl substituents of aromatic compounds is also described.

69 Claims, 3 Drawing Sheets

SYNTHESIS OF (DIBROMOCYCLOBUTA) AROMATIC COMPOUNDS

FIELD OF THE INVENTION

The present invention is directed to methods for the synthesis of (dibromocyclobuta) aromatic compounds, and more particularly to a high yield method of synthesizing bis (dibromocyclobuta) aromatic compounds.

BACKGROUND OF THE INVENTION

Polyacenes are polymers predicted to show industrially important properties including non-linear optics and high-temperature superconductivity, see references 1. Unfortunately, confirmation of the predicted properties has not yet been performed due to the lack of an efficient method to prepare polyacenes.

Cyclobutabenzenes, especially the 7,8-dibromo derivatives 2 (depicted in scheme 1), are valuable synthons for functionalized ortho-quiodimethanes that can be trapped by Diels-Alder reactions. The product of such a reaction is a tetrahydronaphtalene 4 derivative having two cis bromine atoms in the 1 and 4 positions. If the dienophile has two cis hydrogen atoms, and since the Diels-Alder addition is completely endo, these hydrogen atoms end the reaction anti-periplanar to the bromine atoms. Such an orientation facilitates elimination of two HBr molecules to form the corresponding naphtalenic system 6 as described in reference 2 and depicted in scheme 1:

Reference 4 discloses the Diels-Alder condensation of 7,8,9,10-tetrabromo-[1,2][4,5] bicyclobutabenzene 16 with tetracyanoethylene 18, scheme 2:

Reference 4 further discloses the Diels-Alder condensation of two equivalents of 7,8-dibromo cyclobutabenzene 2 with one equivalent of 1,4-benzoquinone 12 to form the bis-adduct that eliminates four equivalents of HBr to form the pentacyclic quinone 14, scheme 3:

Thus, it is expected that of 7,8,9,10-tetrabromo-[1,2][4,5] bicyclobutabenzene 16 can react with benzoquinone 12, in analogy to schemes 2 and 3, to form polyquinone 20, scheme 4:

scheme 4

As further seen in scheme 4, subsequent reduction of polyquinone 20 is expected to yield polyacene 22.

As the use of non-brominated bicyclobutabenzene would result in two saturated centers between the aromatic and quinone moieties, deconjugating the polyacene 20, to synthesize polyquinone 20 it is necessary to use the brominated bicyclobutabenzene, compound 16 or any of the four all-trans tetrabromo isomers thereof. For the Diels-Alder condensation to take place, two bromine atoms on a cyclobutane ring must be in a trans orientation.

A number of methods for synthesizing compound 16 or any of the four all-trans bromo isomers thereof have been disclosed. Reference 5 discloses a synthesis of compound 16 using iodide-mediated ring closure and reports a 2% yield. Reference 4 describes a synthesis of compound 16 using stochiometric amounts of $(Bu_3P)_2Ni(COD)$ and reports a 10% yield.

The bottleneck of the above-proposed route of synthesizing polyacenes such as 22 is the preparation of compounds such as 16. The known methods of synthesizing compound such as 16 suffer from low yields.

It would be highly advantageous to have a high-yield synthesis for (trans dibromocyclobuta) aromatic compounds such as 16.

REFERENCES 1. a. Kivelson, S.; Chapman, O. L. Phys. Rev. 1993, b28, 7326.
   b. Tanaka, K.; Ohzeki, K.; Yata. S. Synth. Metals 1984, 9, 41.
   c. Ozaki, M. Ikedo, Y.; Nagoya, I. Synth. Metals 1989,28 C801.
2. Stanger, A.; Askenazi, N.; Shachter, A.; Blaser, D.; Stellberg, P.; Boese, R. J. Org. Chem. 1996, 61, 2549.
3. Stanger, A.; Askenazi, N.; Boese, R.; Blaser, D.; Stellberg, P.; Chem. Eur. J. 1997, 3, 208.
4. a. Stanger, A.; Shachter, A.; Askenazi, N.; Boese, R. and Stellberg, P. "Nickel Mediated Cyclobutabenzenes Syntheses" in Organic Synthesis via Organometallics OSM 5, Helmchen, G.; Dibo J.; Flubacher, D.; Wiese, B.: Eds. Friedrich Vieweg & Sohn Verlags GmbH, Braunschweig/Wiesbaden, 1997, pp. 59–66.
   b. Shachter, A. "Cyclobutabenzenes: An Entry to a New Synthetic Methodology" D.Sc Thesis, Technion, Haifa, Israel, 1997.
5. Sheferd, M. K. J. Chem. Soc. Perkin Trans I 1988, 961.

SUMMARY OF THE INVENTION

The present invention is directed to a method for the synthesis of a (dibromocyclobuta) aromatic compound by cyclicizing two ortho dibromomethyl substituents of an aromatic moiety. In the product, a bromine atom of an individual cyclobutyl ring is predominantly trans to the other bromine atom of the same cyclobutyl ring.

The method of the present invention is exceptionally suitable for synthesizing aromatic compounds substituted with multiple dibromocyclobutane rings, especially when the substrate includes a 1,2,3,4 or 1,2,4,5 tetra (dibromomethyl) aromatic ring.

Reference 3 describes a nickel-mediated synthesis for the synthesis of hexabromo-tricyclobutabenzene 8, scheme 5:

However, under the conditions of scheme 5, hexabromo-tricyclobutabenzene 8 undergoes butyl ring opening to yield hexabromo-hexaradialene 10, so that the final yield of the reaction is 35% compound 8 and 30% compound 10. In the analogous reaction (not depicted) using 1,2,4,5-tetra dibromomethyl benzene to produce compound 16, only an 8% yield of compound 16 is achieved.

While not wishing to be held to any one theory, it is likely that the low yield of compound 16 using a reaction analogous to that depicted in scheme 5 is a result of decomposition of compound 16 by contact with the nickel mediator, probably to an undefined polymeric material. By modifying the nickel-mediated synthesis described in scheme 5 so as to remove compound 16 formed before decomposition, the method of the present invention provides for an efficient method of producing a (dibromocyclobuta) aromatic compound.

There is provided according to the teachings of the present invention a method for the preparation of an aromatic product having at least one dibromocyclobuta substituent wherein two bromine atoms of an individual cyclobutane ring are in a trans orientation, by dissolving a substrate having an aromatic moiety with at least two ortho dibromomethyl substituents in a reaction solvent (preferably containing DMF). The dissolved substrate is brought in contact with a mediator (preferably nickel, especially as nickel metal powder). Subsequent to cyclization, contact of a cyclicized product with the mediator is limited to prevent product decomposition.

The cyclization reaction is preferably performed at an elevated temperature.

According to a feature of the present invention, limiting the contact of the cyclicized product with the mediator is achieved by using a continuous flow of solvated substrate through a reaction vessel, such as a column, containing substantially immobilized mediator.

According to an additional feature of the present invention, limiting the contact of the cyclicized product with the mediator is achieved by using a two-phase solvent. The first phase is the reaction solvent and the second phase is an extraction solvent, where the cyclicized product is more soluble in the extraction solvent than the substrate is. Preferably the extraction solvent is a mixture of one or more apolar solvents such as straight chain, branched or cyclic alkyl solvents, petrol ethers, hexane, cyclohexane, heptane, methylcyclohexane, octane, nonane, decane, decalin and the such.

Preferably, throughout the reaction, product-containing extraction solvent is removed and replenished from the reaction vessel.

According to the teachings of the present invention there is provided a method for the preparation of a compounds of the general formula:

wherein two bromine atoms of an individual cyclobutane ring are in a trans orientation according to the method described hereinabove, wherein the substrate is and where $R_1$, $R_2$, $R_3$, $R_4$, $R_5$, and R are independently selected from a group consisting of hydrogen, halogen, straight alkyl, branched alkyl, cycloalkyl, substituted alkyl, alkyl aryl, aryl, substituted aryl, heterocycle alkenyl, cycloalkenyl, ether, thioether, amide, amine, alcohol, nitro, thioester, ester, aldehyde and ketone and especially where $R_3$, $R_4$, $R_5$, and $R_6$ are hydrogen atoms.

According to the teachings of the present invention there is also provided a method for the preparation of compounds of the general formula:

wherein two bromine atoms of an individual cyclobutane ring are in a trans orientation according to the method described hereinabove, wherein the substrate is and where $R_1$, $R_2$, $R_3$, $R_4$, $R_5$, and $R_6$ are independently selected from a group consisting of hydrogen, halogen, straight alkyl, branched alkyl, cycloalkyl, substituted alkyl, alkyl aryl, aryl, substituted aryl, heterocycle alkenyl, cycloalkenyl, ether, thioether, amide, amine, alcohol, nitro, thioester, ester, aldehyde and ketone and especially where $R_3$, $R_4$, $R_5$, and $R_6$ are hydrogen atoms.

In the reactions of the present invention described above, it is clear to one skilled in the art that since predominately the trans isomer of the dibromocyclobuta substituent result, then depending on the symmetry of the substrate a mixture of three or four isomers results. The art of separation of the various isomers from a mixture resulting from the present invention is known to one skilled in the art.

The cyclization reaction of the present invention described hereinabove requires an ortho bis(dibromomethyl) aromatic substrate. Thus, the method of the present invention further includes a method of bromination of alkyl groups (especially methyl groups) attached to aromatic moieties (especially benzene derivatives). The method is based on the irradiation with light of an alkyl-substituted aromatic compound in the presence of molecular bromine. Unlike the methods known in the art, the present method is based on performing the reaction in a chloroform-containing solvent.

Thus, there is also provided according to the teachings of the present invention a method of bromination by dissolving a substrate having an alkyl substituent on an aromatic moiety in a chloroform-containing solvent. The dissolved substrate is heated (preferably to the boiling point under reflux conditions) and irradiated with electromagnetic radiation (preferably visible light, and more preferably light including a wavelength that leads to the production of bromine radicals).

The bromination method of the present invention is exceptionally suited for the dibromination of methyl substituents of aromatic moieties to yield the dibromomethyl substituent. The bromination method of the present invention is even more exceptionally suited for the tetrabromination of ortho dimethyl substituents of aromatic moieties to yield the α, α, α', α'-tetrabromo-ortho-xylene moiety.

According to the teachings of the present invention, there is provided a method as described hereinabove for the preparation of a compound of the general formula:

wherein $R_1$ and $R_2$ are independently selected from a group consisting of hydrogen, halogen, straight alkyl, branched alkyl, cycloalkyl, substituted alkyl, alkyl aryl, aryl, substituted aryl, heterocycle alkenyl, cycloalkenyl, ether, thioether, amide, amine, alcohol, nitro, thioester, ester, aldehyde and ketone;

and wherein $R_3$, $R_4$, $R_5$, and $R_6$ are independently selected from a group consisting of hydrogen, fluorine, chlorine, iodine, straight alkyl, branched alkyl, cycloalkyl, substituted alkyl, alkyl aryl, aryl, substituted aryl, heterocycle alkenyl, cycloalkenyl, ether, thioether, amide, amine, alcohol, nitro, thioester, ester, aldehyde and ketone, and especially where $R_3$, $R_4$, $R_5$, and $R_6$ are hydrogen atoms.

Specifically, the present invention provides a method of brominating 1,2,4,5-tetramethylbenzene (durene) to yield 1,2,4,5-tetra (dibromomethyl) benzene as well as a method of brominating 1,2,3,4-tetra methylbenzene to yield 1,2,3,4-tetra (dibromomethyl) benzene, a compound useful for producing [1,2][3,4]tetrabromo bicyclobutabenzene. Clearly, the present invention provides a method for bromination of the derivatives of 1,2,4,5-tetra methylbenzene and 1,2,3,4-tetra (dibromomethyl) benzene to yield the respective brominated derivatives of 1,2,4,5-tetra (dibromomethyl) benzene and [1,2][3,4] tetrabromo bicyclobutabenzene.

BRIEF DESCRIPTION OF THE DRAWINGS

The invention is herein described, by way of example only, with reference to the accompanying drawings, wherein.

DETAILED DESCRIPTION OF THE INVENTION

The present invention is of a method for the synthesis of a (dibromocyclobuta) aromatic compound by cyclicizing an aromatic compound having two ortho dibromomethyl substituents. In the product, a bromine atom of an individual cyclobutyl ring is predominantly trans to the other bromine atom of the same cyclobutyl ring.

The principles of the synthesis of the present invention may be better understood with reference to the drawings, the accompanying description and the examples hereinbelow. Two specific embodiments of the cyclization of the present invention are discussed in detail hereinbelow: using a two-phase solvent or using a continuous flow of substrate through a column-immobilized mediator. It should not be construed that the present invention be limited by the specific chemical reactions and conditions listed.

It is important to note that, as described hereinabove, the method of the present is specifically directed at cyclization of tetra (dibromomethyl) benzenes to yield tricyclic systems. The innovative conditions of the present invention yield only small amounts of the incompletely cyclicized bis (dibromomethyl) cyclobutyl benzene product.

The method of the present invention as discussed herein specifically relates to the cyclization of tetra (dibromomethyl) benzenes, as this is a class of compounds where double cyclization is exceptionally difficult. It is clear to one skilled in the art, however, that the method of the present invention can be applied to the cyclization of any aromatic compound having two ortho dibromomethyl substituents. Methods of cyclization known in the art give a substrate-dependent yield of between 38% and 85%. It is expected that for any given substrate the method of the present invention will give a significantly improved yield when compared to the yields of prior art methods.

Cyclization of ortho bis(dibromomethyl) aromatic compounds using a multi-phase solvent system According to the first embodiment of the present invention, the substrate (an ortho bis (dibromomethyl) aromatic compound) and a mediator are placed in a reaction vessel with a reaction solvent. An extraction solvent is added to the reaction vessel. The reaction mixture is agitated and heated so as to allow cyclization of the substrate. Once cyclization occurs and the product is formed, due to solubility considerations the product enters the extraction solvent and is no longer in contact with the mediator, preventing subsequent decomposition. Methods of isolation and purification of the product from the extraction solvent are well known to one skilled in the art.

Specifically the first embodiment of the present invention includes using nickel, especially in the form of nickel metal powder as a mediator and preferably at least about 0.5 equivalents of mediator to substrate, more preferably at least about 1 equivalents of mediator to substrate, even more preferably at least about 2 equivalents of mediator to substrate, and most preferably at least about 5 equivalents of mediator to substrate.

Any starting concentration (M) of starting material in the reaction solvent can be used, but more often

| between | 0.01 | and | 2, |
|---|---|---|---|
| preferably between | 0.01 | and | 1, |
| more preferably between | 0.01 | and | 0.5, |
| even more preferably between | 0.02 | and | 0.2, |
| and most preferably between | 0.07 | and | 0.1. |

Generally, the substrate of the present invention is soluble in polar solvents such as DMF (dimethylformamide) but only slightly soluble in non-polar solvents. Although not wishing to be held to any one theory, it is believed that the DMF acts as a ligand to stabilize reactive organometallic intermediates (such as a mediator-substrate complex).

It is important to note that using the method of the present invention, the brominated substrate needs not be soluble in the reaction solvent. Although not wishing to be held to any one theory, it is believed that in cases when the substrate is only barely or not soluble in the reaction solvent, the DMF acts to solubilize the reactive organometallic intermediates (such as a mediator-substrate complex). In cases where the substrate is not soluble in the reaction solvent, the amount of substrate above is calculated as actual and not as concentrations, as is clear to one skilled in the art.

Thus, it is desirable that the reaction solvent is any solvent or mixture of solvents containing DMF. Preferably the reaction solvent is so composed that at the beginning of the reaction there are at least 2 equivalents DMF for every equivalent substrate; more preferably there are at least 10 equivalents DMF for every equivalent substrate; even more preferably there are at least 25 equivalents DMF for every equivalent substrate and most preferably there are at least 50 equivalents DMF for every equivalent substrate. If other factors allow, substantially neat DMF can be used as a reaction solvent of the present invention. It is important to note that, generally speaking, the rate of reaction is faster with an increasing DMF component in the reaction solvent.

It is obvious to one skilled in the art that it is ideal that the substrate be barely or not at all soluble in the extraction solvent. It is equally obvious to one skilled in the art that it is also advantageous that the product be slightly or not all soluble in the reaction solvent.

As is clear to one skilled in the art, the greater the solubility of the product in the extraction solvent and the lesser the solubility of the product in the reaction solvent the greater the ultimate yield shall be. Thus ideally: 1) the product is at least slightly soluble, and preferably soluble in the extraction solvent 2) the substrate is substantially insoluble in the extraction solvent 3) the reaction solvent and extraction solvent are substantially immiscible or at least produce a two-phase solvent system.

Despite this, the choice of solvents is not unlimited and each set of substrate and product have different solubility characteristics. Therefore, the minimal requirement of the first embodiment of the present invention to get a reasonable yield is that the extraction solvent is any solvent or mixture of solvents that upon mixing with the reaction solvent yields a solvent system having at least two-phases, an extraction phase and reaction phase, so that the product is at least somewhat soluble in the extraction phase. In such a "minimal" case it is possible to remove product-containing extraction phase from the reaction vessel and to replenish it with fresh extraction solvent. When fresh extraction solvent is added to the reaction, even if the product is less soluble in the extraction phase than in the reaction phase, there is a partition of the product between the two solvent phases. Even if a significant proportion of the product remains in the reaction phase, by continuously removing product-containing extraction phase and adding fresh extraction solvent, product is continuously removed from the reaction even if the product is only slightly soluble in the extraction phase.

Considering the nature of the expected products, a mixture of one or more apolar solvents such as straight chain, branched or cyclic alkyl solvents, petrol ethers, hexane, cyclohexane, heptane, methylcyclohexane, octane, nonane, decane, decalin and the such are preferred-components of an extraction solvent of the present invention.

The reaction temperature can be between 40° and 150° C., preferably between 50° and 120° C., more preferably between 60° and 100° C., even more preferably between 70° and 90° C., and most preferably between 75° and 85° C. As is clear to one skilled in the art, it is preferable that the reaction temperature be lower than the boiling points of both the extraction and the reaction solvents. In the case where it is chosen to use a temperature that is somewhat higher than the boiling point of one of the two solvents, a reflux apparatus can be used to allow condensation and recovery of the evaporated solvents. Due to the fact that when the reaction solvent boils mixing is too vigorous, it is preferable that the reaction temperature be always lower than the boiling point of the reaction solvent.

As is clear to one skilled in the art, the reaction of the present invention can also be performed in a closed system at elevated pressures.

It is necessary to ensure that the mediator-is in effective contact with the reaction solvent and that there be sufficient contact between the reaction solvent and the extraction solvent to allow efficient transfer of cyclicized product from the reaction solvent to the extraction solvent. On the other hand, it is necessary to minimize contact of product-containing extraction solvent with the mediator. Thus, the intensity of agitation, whether thermal or mechanical, needs to be regulated with the aforementioned factors in mind.

As noted above, for the reaction yield be maximal, it is preferred that product-containing extraction phase be removed from the reaction vessel during the reaction, preferably continuously removed. When the product-containing extraction phase is removed from the reaction vessel during the reaction, it is preferable to concurrently replenish the extraction phase by adding a substantially equal amount of fresh extraction solvent.

It is preferable that the extraction solvent be less dense then the reaction solvent, so that product containing extraction solvent can be easily collected from the top of the reaction vessel without interference from mediator which tends to collect at the bottom of the reaction vessel.

Figure 1:
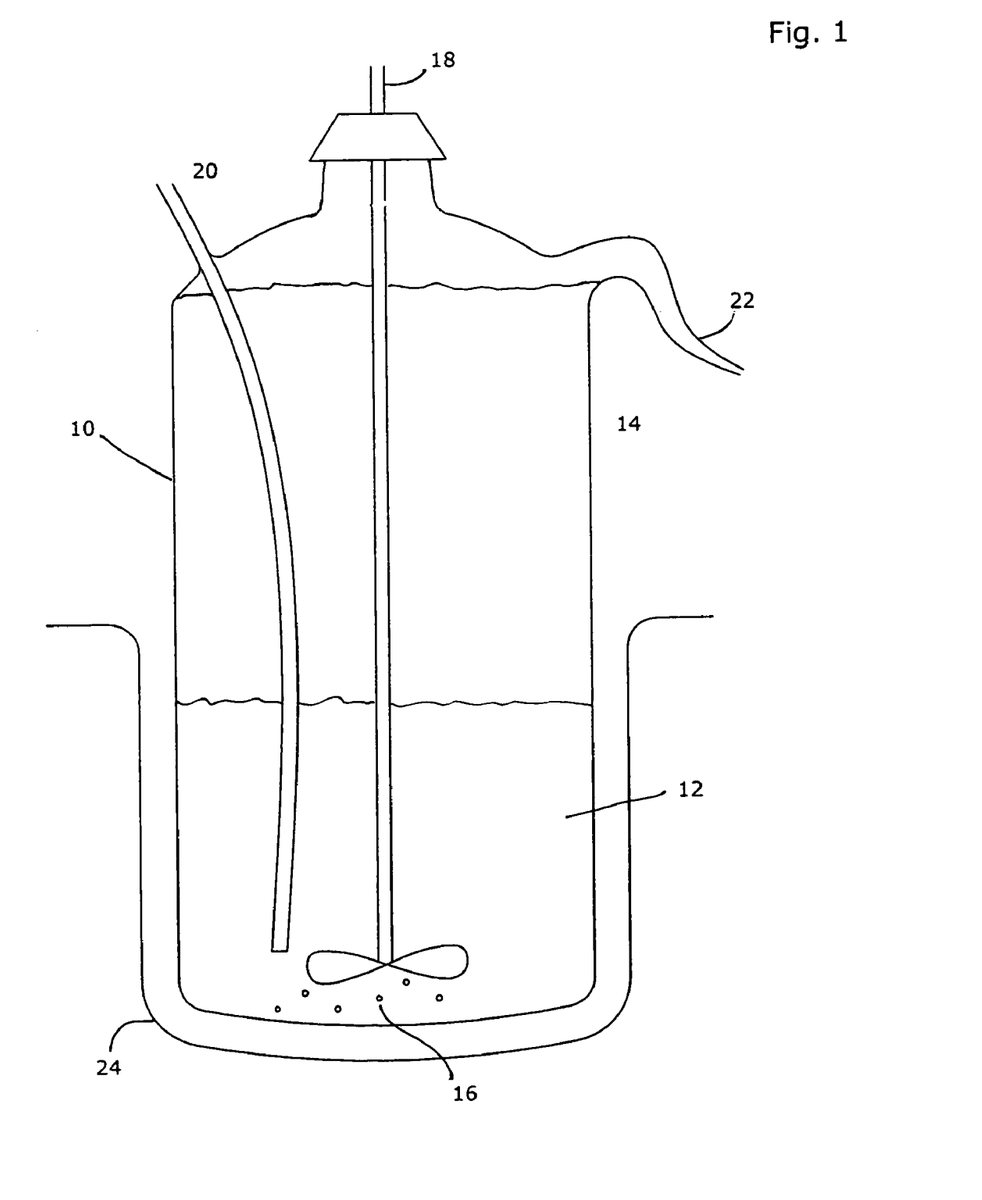
FIG. 1 is of a device useful in implementing the first embodiment of the present invention.

In FIG. 1, a reaction vessel 10 useful for implementing the first embodiment of the method of the present invention is depicted. Reaction solvent 12 (DMF) is denser than extraction solvent 14 (heptane). Due to its density, a mediator powder 16 remains in reaction solvent 12. Mechanical stirrer 18 causes sufficient agitation to prevent settling of mediator powder 16 at the bottom of vessel 10, ensuring contact between mediator powder 16 and substrate dissolved in reaction solvent 12. Additional extraction solvent is continuously added through feed tube 20. The addition of extraction solvent through feed tube 20 causes a continuous overflow of product-containing extraction solvent through port 22. Overflow is collected for subsequent product isolation. Heating is provided by oil bath 24.

It is also possible to implement the first embodiment of the present invention when the extraction solvent is denser then the reaction solvent, the excess extraction solvent is collected from the bottom of the reaction vessel. In such a case care is taken to prevent insoluble material such as the mediator from being removed from the reaction along with the product.

Figure 2:
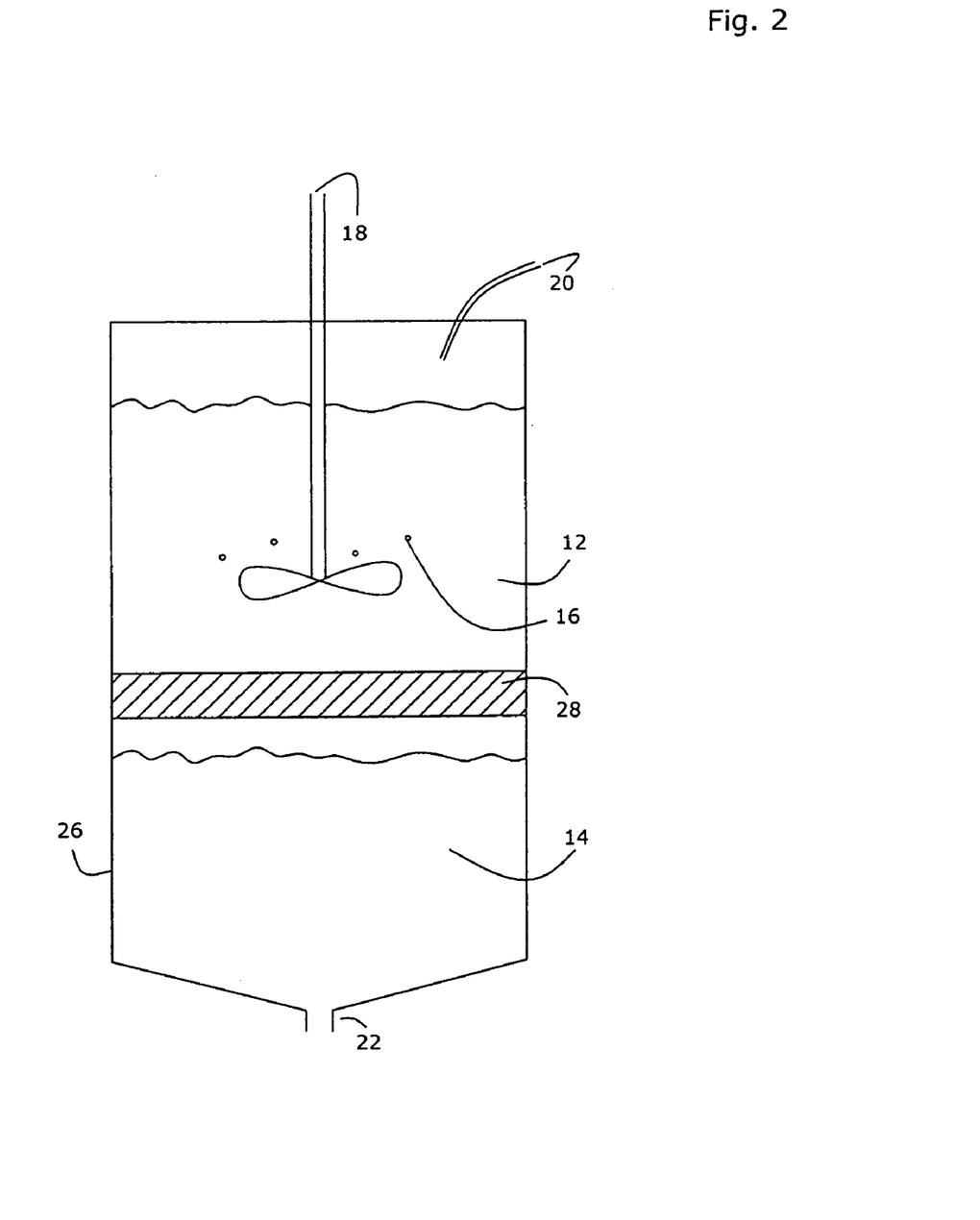
FIG. 2 is of a device also useful in implementing the first embodiment of the present invention.

In FIG. 2, a reaction vessel 26 useful for implementing the first embodiment of the method of the present invention is depicted. Reaction solvent 12 is less dense than extraction solvent 14. Due to the presence of a porous sintered glass layer 28 mediator powder 16 remains in reaction solvent 12 although reaction solvent can freely flow through glass layer 28 to make contact with extraction solvent 14. Mechanical stirrer 18 causes sufficient agitation to prevent settling of mediator powder 16 on glass layer 28, ensuring contact between mediator powder 16 and substrate dissolved in reaction solvent 12. Product containing extraction solvent 14 is continuously drained through port 22. Additional extraction solvent is continuously added through feed tube 20 to maintain a sufficient amount of solvent in vessel 26.

Cyclization of ortho bis(dibromomethyl)aromatic Compounds Using Continuous-Flow Through Column-Immobilized Mediator According to the second embodiment of the present invention, the substrate (an ortho bis(dibromomethyl) aromatic compound), dissolved in a reaction solvent, is streamed through a column (or functionally equivalent device) containing an immobilized mediator, preferably nickel, especially as nickel metal powder. As the substrate flows through the column, contact of substrate with the mediator leads to formation of the desired product. Preferably the column is heated to allow efficient cyclization of the substrate. Clearly, the interdependence of the reaction conditions, such as the exact nature of the reaction solvent, the flow rate of flow, the condition of the mediator the nature of the substrate, the length of the column and the temperature necessitates optimization of every specific reaction. As is clear to one skilled in the art, optimization involves identifying a set of conditions that lead to maximal product formation yet minimal product contact with the mediator.

Specifically the second embodiment of the present invention includes using any starting concentration (M) of starting material in the reaction solvent, but more often

| between | 0.01 | and | 2, |
| preferably between | 0.01 | and | 1, |
| more preferably between | 0.01 | and | 0.5, |
| even more preferably between | 0.02 | and | 0.2, |
| and most preferably between | 0.05 | and | 0.08. |

The reaction solvent chosen is as specified hereinabove for the first embodiment of the present invention.

The rate of flow of reaction solvent through the reaction column can be anything, but more often (in units of seconds to pass one column-volume of solvent)

| between | 1 | and | 560, |
| preferably between | 5 | and | 240, |
| more preferably between | 10 | and | 120, |
| even more preferably between | 15 | and | 45, |
| and most preferably between | 18 | and | 22. |

The reaction temperature can be between 40° and 160° C., preferably between 80° and 160° C., more preferably between 100° and 140° C., even more preferably between 110° and 130° C., and most preferably between 115° and 125° C.

Methods of isolation and purification of the product from the product-containing reaction solvent collected from the terminal end of the column is clear to one skilled in the art.

Figure 3:
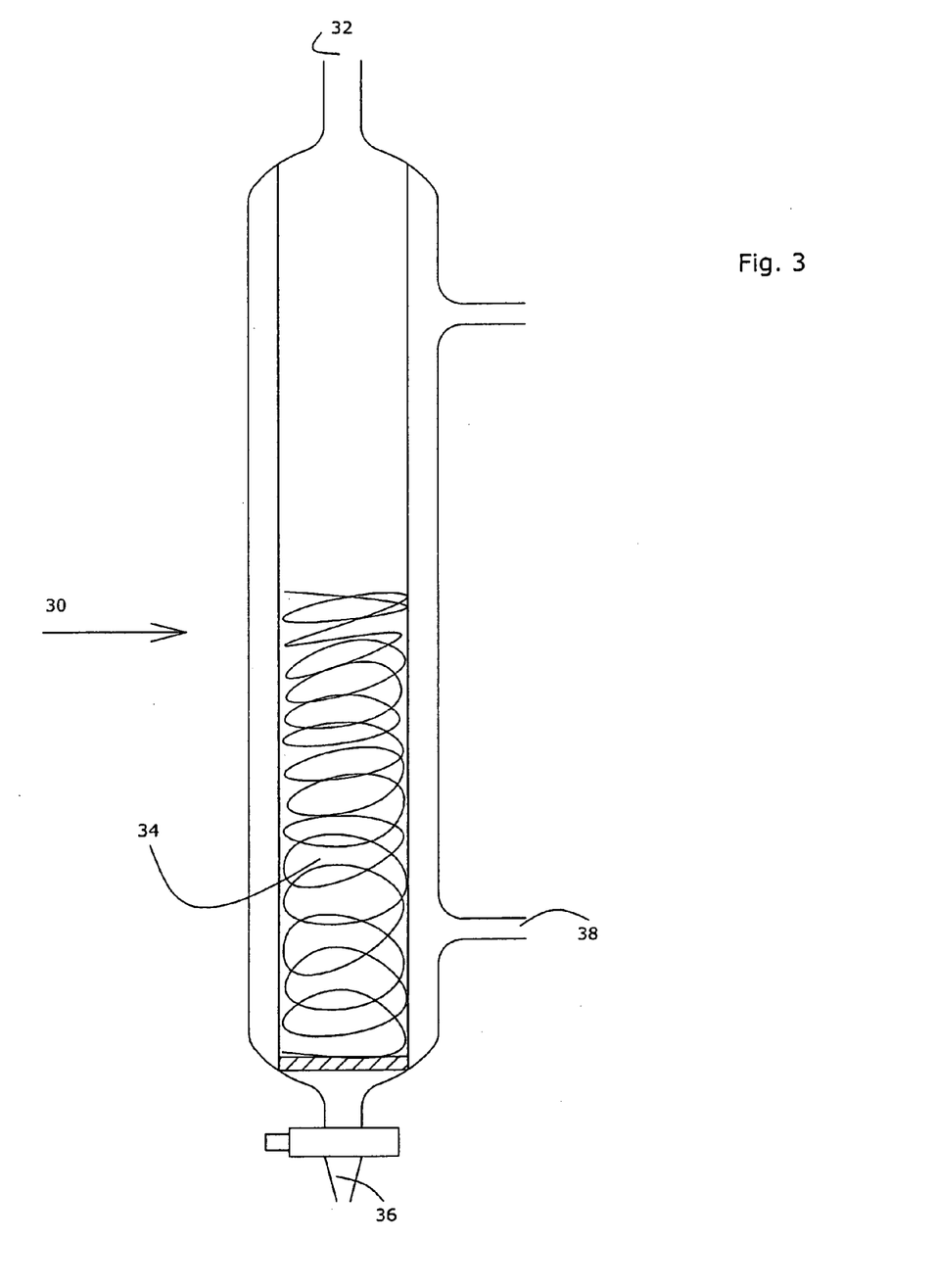
FIG. 3 is of a device useful in implementing the second embodiment of the present invention.

A column 30, suitable for realizing the second embodiment of the present invention is depicted in FIG. 3. Substrate containing reaction solvent is introduced through inlet 32 of column 30. As the reaction solvent flows through column 30, substrate reacts to yield product according to the method of the present invention by interaction with immobilized mediator powder 34. In FIG. 3, mediator powder 34 is immobilized in glass wool. Product-containing solvent drips out through stopcock 36 and is collected. Column 30 is jacketed, allowing heating of solvent inside column 30 by the introduction of a heated liquid through port 38.

Bromination of Alkyl Groups Attached to Aromatic Compounds

Most generally, bromination according to the method of the present invention is a light-catalyzed bromination of alkyl groups attached to an aromatic substrate dissolved in chloroform at reflux by addition of molecular bromine.

An aromatic compound with at least one alkyl group is dissolved in chloroform and placed in a reaction vessel configured so as to allow reflux of the solution. The solution is allowed to reflux and irradiated with light; $Br_2$ is added in portions to the refluxing chloroform solution. After the reaction is complete, reflux and irradiation are stopped and the brominated product isolated from the chloroform.

Preferably, sunlight or a sunlight lamp is used to irradiate the reaction mixture. More preferably, light containing a wavelength sufficient to produce bromine radicals is used.

The starting concentration (M) of starting material in the chloroform solvent can be anything, but more often

| between | 0.01 | and | 2, |
| preferably between | 0.01 | and | 1, |
| more preferably between | 0.01 | and | 0.5, |
| even more preferably between | 0.02 | and | 0.2, |
| and most preferably between | 0.07 | and | 0.1. |

Isolation and purification of the product can be performed using any of the methods known to one skilled in the art.

It is important to note that in the art, for example, a 76% yield of 1,2,4,5-tetra (dibromomethyl) benzene can be achieved by reacting durene under similar conditions using $CCl_4$ as a reaction solvent. Unexpectedly and unpredictably, a 96% yield is achieved using the method of the present invention that is using chloroform as a solvent.

SPECIFIC SYNTHETIC EXAMPLES

Bromination of Durene to Yield Octabromodurene $Br_2$ (46.6 ml, 0.907 mole) was added dropwise to a refluxing solution of durene (2.964 gr., 0.022 mol) in chloroform (220 ml). The heat and light needed for the reaction were supplied by a 375 W sunlight lamp. The end of the reaction (after about 5 days) was determined by $^1H$ NMR. The reaction mixture was cooled to room temperature and neutralized with a 5% aqueous $NaHCO_3$ solution. The solid product was filtered, washed with a 10% thiosulphate solution, water and methanol. After the methanol wash the product was dried in high vacuum until constant weight achieved. Obtained were 16.095 gr. (96% yield) of octabromodurene.

Cyclization of Octabromodurene

Example A

Two-Phase Solvent

Metallic nickel powder (1.157 gr., 0.0197 mol), octabromodurene (1.507 gr., 1.969 mmol) and DMF (26 ml) were placed in a 50 mol reaction vessel. Heptane was added to fill the vessel. The reaction mixture was heated to 80° C. and additional heptane was introduced using a syringe pump at a rate of 10 ml/hour. The heptane overflow was collected. DMF was added from time to time to compensate for its loss as under the semi-improvised conditions used some DMF "escaped" to the heptane phase. After 9 days the collected heptane phase was evaporated using vacuum. An amount of chloroform sufficient to dissolve the product-containing residue was added and adsorbed, onto 1 gram Florisil® (60–100 mesh activated magnesium silicate, CAS nr. 1343-88-0) and chloroform removed under vacuum. The product adsorbed on the Florisil® was placed on top of an open topped Florisil®-packed chromatographic column and eluted using chloroform. The chloroform solution was washed with 5% HCl, 5% $NaHCO_3$, water, and dried over $MgSO_4$. A 22% yield of [1,2][4,5] tetrabromo bicyclobutabenzene 16 was obtained.)

Example B

Immobilized Nickel

Metallic nickel powder (6.5 gr.) spread on glass wool was placed in a jacketed column (10 mm internal diameter) so that the height of the nickel on glass wool was 5 cm. The column was heated to 120° C., and a solution of octabromodurene (1.54 gr., 2 mmol) in warm DMF (32 ml) was allowed to pass through the column at a rate of 1 drop/sec. After all the octabromodurene solution was added, neat EMT was introduced into the column at a rate of 1 drop/sec until the solution dripping from the column was colorless. The total amount DMF added was approximately 70 ml. The DMF was evaporated and the product isolated as described in Example A. A 28% yield of tetrabromo bicyclobutabenzene 16 was obtained.

Bromination of 1.2,3,4-tetramethyl Benzene to Yield 1.2.3.4-tetra (Dibromomethyl) Benzene Br₂ (46.6 ml, 0.907 mol) is added dropwise to a refluxed solution of 1,2,3,4-tetramethylbenzene (2.964 gr., 0.022 mol) in chloroform (220 ml). The heat and light needed for the reaction are supplied by a 375 W sunlight lamp. The end of the reaction is determined by ¹H NMR. The reaction mixture is cooled to room temperature, and then neutralized using a 5% aqueous HaHCO₃ solution. The solid product is filtered, washed with 10% thiosulphate solution, water and methanol, and dried in high vacuum until constant weight achieved. Obtained is 1,2,3,4-tetrakis dibromomethyl benzene.

Cyclization of Octabromo 1,2,3,4-tetramethylbenzene

Example C

Two-Phase Solvent

Metallic nickel powder (1.157 gr., 0.0197 mol), tetrakis (dibromomethyl) benzene (1.507 gr., 1.969 mmol) and DMF (26 ml) are placed in a 50 ml reaction vessel and heptane is added to fill the vessel. The reaction mixture is heated to 80° C. and heptane is introduced by a syringe pump at a 2–10 ml/hour rate. The overflow is collected.

Some DMF is added from time to time to compensate for loss of DMF to the heptane phase. The collected heptane is evaporated in vacuum. Chloroform and Florisil® are added to the residue, and dried in vacuum. The product adsorbed on the Florisil® is placed on top of an open topped Florisil®-packed chromatographic column, and the product eluted with chloroform. The chloroform solution is washed with 5% HCl, 5% NaHCO₃, water, and dried over MgSO₄. Obtained is tetrabromo [1,2][3,43 ]bicyclobutabenzene.

Example D

Immobilized Nickel

Metallic nickel powder (6.5 gr.) spread on glass wool is placed in a jacketed column (10 mm internal diameter) so that the height of the nickel on glass wool is 5 cm. The column is heated to 120° C., and a solution of tetrakis (dibromomethyl)benzene (1.54 gr., 2 mmol) in warm DMF (32 ml) is allowed to pass through the column in the rate of 1 drop/sec. The column is washed with DMF until the solution dripping from the column is colorless. The DMF is evaporated and the product worked up as described in Example C. Obtained is tetrabromo-[1,2][3,4] bicyclobutabenzene.

What is claimed is:

1. A method for the preparation of a product, the product being an aromatic compound with at least one dibromocyclobuta substituent, the method comprising:
   a. providing a substrate having an aromatic moiety including at least two ortho dibromomethyl substituents;
   b. dissolving said substrate in a reaction solvent to produce a dissolved substrate;
   c. providing a mediator;
   d. bringing said dissolved substrate in contact with said mediator, in a reaction mixture, to mediate a cyclization reaction; and
   e. selectively reducing contact of the product, produced by said cyclization reaction, with said mediator, in said reaction mixture.

2. The method of claim 1 wherein said mediator includes nickel.

3. The method of claim 2 wherein said mediator includes nickel metal powder.

4. The method of claim 1 wherein said aromatic moiety of said substrate includes at least four dibromomethyl substituents, each one of said at least four dibromomethyl substituents being ortho to at least one other of said at least four dibromomethyl substituents.

5. The method of claim 1 wherein said reaction solvent includes DMF (dimethyl formamide).

6. The method of claim 5 wherein said reaction solvent includes at least about 2 equivalents of said DMF for every 1 equivalent of said substrate.

7. The method of claim 6 wherein said reaction solvent includes at least about 10 equivalents of said DMF for every 1 equivalent of said substrate.

8. The method of claim 7 wherein said reaction solvent includes at least about 25 equivalents of said DMF for every 1 equivalent of said substrate.

9. The method of claim 8 wherein said reaction solvent includes at least about 50 equivalents of said DMF for every 1 equivalent of said substrate.

10. The method of claim 5 wherein said reaction solvent is substantially neat DMF.

11. The method of claim 1 wherein said limiting of subsequent contact includes substantially immobilizing said mediator in a reaction vessel and bringing said dissolved substrate in temporary contact with said immobilized mediator by flowing said dissolved substrate through said mediator in said reaction vessel.

12. The method of claim 11, wherein a temperature of said reaction solvent in said reaction vessel is between 40° and 160° C.

13. The method of claim 12 wherein said temperature is between 80° C. and 160° C.

14. The method of claim 13 wherein said temperature is between 100° C. and 140° C.

15. The method of claim 11 wherein a starting concentration of said substrate in said reaction solvent is between 0.01 M and 2 M.

16. The method of claim 15 wherein a starting concentration of said substrate in said reaction solvent is between 0.01 M and 1 M.

17. The method of claim 16 wherein a starting concentration of said substrate in said reaction solvent is between 0.01 M and 0.5 M.

18. The method of claim 17 wherein a starting concentration of said substrate in said reaction solvent is between 0.02 M and 0.2 M.

19. The method of claim 17 wherein a starting concentration of said substrate in said reaction solvent is between 0.05 M and 0.08 M.

20. The method of claim 1 wherein said reducing of said contact includes performing said cyclization reaction in a presence of an extraction solvent in said reaction mixture, said extraction solvent selected so that upon mixing of said extraction solvent and said reaction solvent, a solvent system having at least two co-existing phases, a first reaction phase and a second extraction phase, is formed, such that the product is at least slightly soluble in said second extraction phase.

21. The method of claim 20 wherein said reducing of said contact further includes removing a portion of said second extraction phase containing the product from said solvent system.

22. The method of claim 21 wherein said reducing of said contact further includes adding fresh extraction solvent to said solvent system so as to compensate for said removing of said portion of said product-containing second extraction phase.

23. The method of claim 22 wherein said removing is continuous.

24. The method of claim 20 wherein said extraction solvent is less dense than said reaction solvent.

25. The method of claim 20 wherein said extraction solvent includes a mixture of individual solvents.

26. The method of claim 20 wherein said extraction solvent includes at least one apolar solvent.

27. The method of claim 26 wherein said extraction solvent includes at least one of the apolar solvents from the group consisting of straight chain alkanes, branched alkanes, cyclic alkanes, petrol ethers, hexane, cyclohexane, heptane, methylcyclohexane, octane, nonane, decane and decalin.

28. The method of claim 20 wherein said extraction solvent is further selected so as to be substantially immiscible with said reaction solvent and wherein said substrate is substantially insoluble in said extraction solvent.

29. The method of claim 20, wherein a temperature of said reaction phase is between 40° C. and 150° C.

30. The method of claim 29 wherein said temperature is between 50° C. and 120° C.

31. The method of claim 30 wherein said temperature is between 60° C. and 100° C.

32. The method of claim 30 wherein said temperature is between 70° C. and 90° C.

33. The method of claim 32 wherein said temperature is between 75° C. and 85° C.

34. The method of claim 20, wherein a temperature of said first reaction phase is substantially a boiling temperature of said second extraction phase.

35. The method of claim 20, wherein a temperature of said first reaction phase is substantially a boiling temperature of said first reaction phase.

36. The method of claim 20 wherein at a start of said reaction there is at least about 0.5 equivalents mediator relative to said substrate.

37. The method of claim 20 wherein at a start of said reaction there is at least about 1 equivalents mediator relative to said substrate.

38. The method of claim 20 wherein at a start of said reaction there is at least about 2 equivalents mediator relative to said substrate.

39. The method of claim 20 wherein at a start of said reaction there is at least about 5 equivalents mediator relative to said substrate.

40. The method of claim 20 wherein a starting concentration of said substrate in said first reaction phase is between 0.01 M and 2 M.

41. The method of claim 20 wherein a starting concentration of said substrate in said first reaction phase is between 0.01 M and 1 M.

42. The method of claim 20 wherein a starting concentration of said substrate in said first reaction phase is between 0.01 M and 0.5 M.

43. The method of claim 20 wherein a starting concentration of said substrate in said first reaction phase is between 0.02 M and 0.2 M.

44. The method of claim 20 wherein a starting concentration of said substrate in said first reaction phase is between 0.07 M and 0.1 M.

45. A method for the preparation of a compound of the formula according to claim 1, wherein two bromine atoms of an individual cyclobutane ring are in a trans orientation, according to the method of claim 1 wherein said substrate is where $R_1$, $R_2$, $R_3$, $R_4$, $R_5$, and $R_6$ are independently selected from a group consisting of hydrogen, halogen, straight alkyl, branched alkyl, cycloalkyl, substituted alkyl, alkyl aryl, aryl, substituted aryl, heterocycle alkenyl, cycloalkenyl, ether, thioether, amide, amine, alcohol, nitro, thioester, ester, aldehyde and ketone.

46. A compound of claim 45 where $R_3$, $R_4$, $R_5$, and $R_6$ are hydrogen atoms.

47. A method for the preparation of a compound of the formula:

according to claim 1, wherein two bromine atoms of an individual cyclobutane ring are in a trans orientation, according to the method of claim 1 wherein said substrate is and where $R_1$, $R_2$, $R_3$, $R_1$, $R_5$, and $R_6$ are independently selected from a group consisting of hydrogen, halogen, straight alkyl, branched alkyl, cycloalkyl, substituted alkyl, alkyl aryl, aryl, substituted aryl, heterocycle alkenyl, cycloalkenyl, ether, thioether, amide, amine, alcohol, nitro, tbioester, ester, aldehyde and ketone.

48. A method of claim 47 where $R_3$, $R_4$, $R_5$, and $R_6$ are hydrogen atoms.

49. A method for bromination comprising
   a. providing a substrate having an aromatic moiety with at least one alkyl substituent;
   b. dissolving said substrate in chloroform;
   c. introducing said substrate dissolved in said solvent, and a bromine source, to a reaction vessel, to form a reaction mixture;
   d. heating said reaction; and
   e. irradiating said reaction mixture with electromagnetic radiation so as to effect the bromination of said substrate.

50. The method of claim 49 wherein said substrate has an aromatic moiety with at least two ortho alkyl substituents.

51. The method of claim 49 wherein said electromagnetic radiation includes components having visible light wavelengths.

52. The method of claim 49 wherein said solvent includes at least 90% by weight of chloroform.

53. The method of claim 52 wherein said solvent includes at least 97% by weight of chloroform.

54. The method of claim 53 wherein said solvent comprises substantially neat chloroform.

55. The method of claim 49 wherein said heating is to a boiling point of said solvent.

56. The method of claim 49 wherein a starting concentration of said substrate in said reaction solvent is between 0.01 M and 2 M.

57. The method of claim 49, wherein a starting concentration of said substrate in said reaction solvent is between 0.01 M and 1 M.

58. The method of claim 49, wherein a starting concentration of said substrate in said reaction solvent is between 0.01 M and 0.5 M.

59. The method of claim 49, wherein a starting concentration of said substrate in said reaction solvent is between 0.02 M and 0.2 M.

60. The method of claim 49, wherein a starting concentration of said substrate in said reaction solvent is between 0.07 M and 0.1 M.

61. The method of claim 49 wherein at least one of said at least one alkyl substituent is a methyl substituent.

62. A method for the preparation of a compound of the general formula:

according to the method of claim 49 wherein $R_1$ and $R_2$ are independently selected from a group consisting of hydrogen, halogen, straight alkyl, branched alkyl, cycloalkyl, substituted alkyl, alkyl aryl, aryl, substituted aryl, heterocycle alkenyl, cycloalkenyl, ether, thioether, amide, amine, alcohol, nitro, thioester, ester, aldehyde and ketone; and wherein $R_3$, $R_4$, $R_5$, and $R_6$ are independently selected from a group consisting of hydrogen, fluorine, chlorine, iodine, straight alkyl, branched alkyl, cycloalkyl, substituted alkyl, alkyl aryl, aryl, substituted aryl, heterocycle alkenyl, cycloalkenyl, ether, thioether, amide, amine, alcohol, nitro, thioester, ester, aldehyde and ketone.

63. The method of claim 62 where $R_3$, $R_4$, $R_5$, and $R_6$ are hydrogen atoms.

64. A method for the preparation of a compound of the general formula:

according to the method of claim 49 wherein $R_1$ and $R_2$ are independently selected from a group consisting of hydrogen, halogen, straight alkyl, branched alkyl, cycloalkyl, substituted alkyl, alkyl aryl, aryl, substituted aryl, heterocycle alkenyl, cycloalkenyl, ether, thioether, amide, amine, alcohol, nitro, thioester, ester, aldehyde and ketone; and wherein $R_3$, $R_4$, $R_5$, and $R_6$ are independently selected from a group consisting of hydrogen, fluorine, chlorine, iodine, straight alkyl, branched alkyl, cycloalkyl, substituted alkyl, alkyl aryl, aryl, substituted aryl, heterocycle alkenyl, cycloalkenyl, ether, thioether, amide, amine, alcohol, intro, thioester, ester, aldehyde and ketone.

65. The method of claim 64 where $R_3$, $R_4$, $R_5$, and $R_6$ are hydrogen atoms.

66. The method of claim 1, wherein said reducing contact of the product with said mediator is selective with respect to said substrate.

67. The method of claim 1, wherein said reducing contact of the product with said mediator is with respect to a contact of the product with said mediator in an analogous batch reaction.

68. The method of claim 20, wherein said extraction solvent is further selected so as to be substantially immiscible with said reaction solvent.

69. The method of claim 20, wherein said substrate is substantially insoluble in said extraction solvent.

* * * * *

UNITED STATES PATENT AND TRADEMARK OFFICE
CERTIFICATE OF CORRECTION

| | |
|---|---|
| PATENT NO. | : 7,138,554 B2 |
| APPLICATION NO. | : 10/472180 |
| DATED | : November 21, 2006 |
| INVENTOR(S) | : Stanger |

It is certified that error appears in the above-identified patent and that said Letters Patent is hereby corrected as shown below:

Title page #63

Related U.S. Application Data: Provisional application No. 60/297,766, filed on June 14, 2001 should be added.

Claim 45, column 18 should be corrected as follows:

Line 60: change "cycloallcyl" to --cycloalkyl--

Claim 49{d}, column 19 should be corrected as follows:

Line 41: insert --mixture-- between " reaction" and ";"

Signed and Sealed this

Eighth Day of May, 2007

JON W. DUDAS
*Director of the United States Patent and Trademark Office*